US008410082B2

(12) United States Patent
Liu et al.

(10) Patent No.: US 8,410,082 B2
(45) Date of Patent: Apr. 2, 2013

(54) FLUORINATED DIARYL UREA DERIVATIVES

(75) Inventors: Julie F. Liu, Lexington, MA (US);
Roger D. Tung, Lexington, MA (US);
Scott L. Harbeson, Cambridge, MA (US)

(73) Assignee: Concert Pharmaceuticals, Inc., Lexington, MA (US)

( * ) Notice: Subject to any disclaimer, the term of this patent is extended or adjusted under 35 U.S.C. 154(b) by 0 days.

(21) Appl. No.: 13/320,646

(22) PCT Filed: May 20, 2010

(86) PCT No.: PCT/US2010/035655
§ 371 (c)(1),
(2), (4) Date: Jun. 5, 2012

(87) PCT Pub. No.: WO2010/135579
PCT Pub. Date: Nov. 25, 2010

(65) Prior Publication Data
US 2012/0237474 A1 Sep. 20, 2012

Related U.S. Application Data

(60) Provisional application No. 61/216,943, filed on May 22, 2009.

(51) Int. Cl.
*A61K 31/56* (2006.01)
*A61K 31/44* (2006.01)
*A61K 38/21* (2006.01)
*A61K 39/00* (2006.01)
*A61K 33/24* (2006.01)
*C07D 213/78* (2006.01)

(52) U.S. Cl. .... 514/171; 514/350; 424/85.2; 424/133.1; 424/649; 546/298

(58) Field of Classification Search .................. 514/171, 514/350, 351; 424/85.2, 133.1, 649; 546/298
See application file for complete search history.

(56) References Cited

U.S. PATENT DOCUMENTS

| | | | |
|---|---|---|---|
| 6,221,335 | B1 | 4/2001 | Foster |
| 6,440,710 | B1 | 8/2002 | Keinan et al. |
| 6,603,008 | B1 | 8/2003 | Ando et al. |
| 7,517,990 | B2 | 4/2009 | Ito et al. |
| 2007/0082929 | A1 | 4/2007 | Gant et al. |
| 2007/0197695 | A1 | 8/2007 | Potyen et al. |
| 2008/0103122 | A1 | 5/2008 | Veltri |

FOREIGN PATENT DOCUMENTS

| | | |
|---|---|---|
| WO | 95/26325 A2 | 10/1995 |
| WO | WO2005/009961 | 2/2005 |
| WO | 2007/118651 A1 | 10/2007 |
| WO | WO2010/019701 | 2/2010 |
| WO | 2010135579 A1 | 11/2010 |

OTHER PUBLICATIONS

Pleiss, U., et al., Syntheses f [2H3, 15N], [14C]Nexavar and its Labeled Metabolites, Journal of Labelled Compounds and Radiopharmaceuticals, (2006), 49(7), 603-613.
Foster, A.B., Deuterium Isotope Effects in the Metabolism of Drugs and Xenobiotics: Implications for Drug Design, Advances in Drug Research, (1985), 14, 1-40.
Kushner, DJ, et al., Pharmacological Uses and Perspectives of Heavy Water and Deuterated Compounds, Canadian Journal of Physiology and Pharmacology, (1999), 77(2), 79-88.
Dumont,et al., Prospects in the Use of Deuterated Molecules as Therapeutic Agents, Revue Ire, Institut National Des Radioelements, (1982), 6(4), 2-10.
International Search Report of corresponding PCT/US2010/035655 Jul. 20, 2010.
Written Opinion of corresponding PCT/US2010/035655 Jul. 20, 2010.
Baille, T. A., "The Use of Stable Isotopes in Pharmacological Research," Pharmacological Reviews, 33(2): 81-132 (1981).
Browne, T. R., "Stable Isotope Techniques in Early Drug Development: An Economic Evaluation," J. Clin. Pharmacol., 38: 213-220 (1998).
Cherrah, Y., et al., "Study of Deuterium Isotope Effects on Protein Binding by Gas Chromatography/Mass Spectrometry. Caffeine and Deuterated Isotopomers," Biomedical and Environmental Mass Spectrometry, 14: 653-657 (1987).
Dyck, L. E., et al., "Effects of Deuterium Substitution on the Catabolism of Beta-Phenylethylamine: An In Vivo Study," Journal of Neurochemistry, 46(2): 399-404 (1986).
Foster, A. B., "Deuterium Isotope Effects in Studies of Drug Metabolism," Trends in Pharmacological Sciences, 5: 524-527 (1984).
Gouyette, A., "Synthesis of Deuterium-labelled Elliptinium and its Use in Metabolic Studies," Biomedical and Environmental Mass Spectrometry, 15: 243-247 (1988). Haskins, N. J., "The Application of Stable Isotopes in Biomedical Research," Biomedical Mass Spectrometry, 9(7): 269-277 (1982).
Honma S., et al., "The Metabolism of Roxatidine Acetate Hydrochloride," Drug Metabolism and Disposition, 15(4): 551-559 (1987).
Pieniaszek, H. J., et al., "Moricizine Bioavailability via Simultaneous, Dual, Stable Isotope Administration: Bioequivalence Implications," J. Clin. Pharmacol., 39: 817-825 (1999).

(Continued)

*Primary Examiner* — Raymond Henley, III
(74) *Attorney, Agent, or Firm* — McCarter & English LLP; Steven G. Davis

(57) ABSTRACT

This invention relates to novel diaryl urea compounds, their derivatives, and pharmaceutically acceptable salts thereof. This invention also provides compositions comprising a compound of this invention and the use of such compositions in methods of treating diseases and conditions that are beneficially treated by administering an inhibitor of multiple kinases.

10 Claims, No Drawings

OTHER PUBLICATIONS

Tonn G. R., et al., "Simultaneous Analysis of Diphenhydramine and a Stable Isotope Analog (2H10) Diphenhydramine Using Capillary Gas Chromatography with Mass Selective Detection in Biological Fluids from Chronically Instrumented Pregnant Ewes," Biological Mass Spectrometry, 22: 633-642 (1993).

Wolen, R. L., "The Application of Stable Isotopes to Studies of Drug Bioavailability and Bioequivalence," J. Clin. Pharmacol., 26: 419-424 (1986).

Fisher, M.B. et al., "The Complexities Inherent in Attempts to Decrease Drug Clearance by Blocking Sites of CYP-Mediated Metabolism," Curr. Opin. Drug Discov. Devel., 9(1):101-109 (2006).

STIVARGA®, FDA Label, Sep. 2012.

FLUORINATED DIARYL UREA DERIVATIVES

RELATED APPLICATIONS

This application is the U.S. National Stage filed under 35 USC 371 of PCT/US2010/035655, filed May 20, 2010, which claims the benefit of U.S. Provisional Application No. 61/216,943, filed May 22, 2009. The entire teachings of U.S. Provisional Application No. 61/216,943 are incorporated herein by reference.

BACKGROUND OF THE INVENTION

Many current medicines suffer from poor absorption, distribution, metabolism and/or excretion (ADME) properties that prevent their wider use or limit their use in certain indications. Poor ADME properties are also a major reason for the failure of drug candidates in clinical trials. While formulation technologies and prodrug strategies can be employed in some cases to improve certain ADME properties, these approaches often fail to address the underlying ADME problems that exist for many drugs and drug candidates. One such problem is rapid metabolism that causes a number of drugs, which otherwise would be highly effective in treating a disease, to be cleared too rapidly from the body. A possible solution to rapid drug clearance is frequent or high dosing to attain a sufficiently high plasma level of drug. This, however, introduces a number of potential treatment problems such as poor patient compliance with the dosing regimen, side effects that become more acute with higher doses, and increased cost of treatment. A rapidly metabolized drug may also expose patients to undesirable toxic or reactive metabolites.

Another ADME limitation that affects many medicines is the formation of toxic or biologically reactive metabolites. As a result, some patients receiving the drug may experience toxicities, or the safe dosing of such drugs may be limited such that patients receive a suboptimal amount of the active agent. In certain cases, modifying dosing intervals or formulation approaches can help to reduce clinical adverse effects, but often the formation of such undesirable metabolites is intrinsic to the metabolism of the compound.

In some select cases, a metabolic inhibitor will be co-administered with a drug that is cleared too rapidly. Such is the case with the protease inhibitor class of drugs that are used to treat HIV infection. The FDA recommends that these drugs be co-dosed with ritonavir, an inhibitor of cytochrome P450 enzyme 3A4 (CYP3A4), the enzyme typically responsible for their metabolism (see Kempf, D. J. et al., Antimicrobial agents and chemotherapy, 1997, 41(3): 654-60). Ritonavir, however, causes adverse effects and adds to the pill burden for HIV patients who must already take a combination of different drugs. Similarly, the CYP2D6 inhibitor quinidine has been added to dextromethorphan for the purpose of reducing rapid CYP2D6 metabolism of dextromethorphan in a treatment of pseudobulbar affect. Quinidine, however, has unwanted side effects that greatly limit its use in potential combination therapy (see Wang, L et al., Clinical Pharmacology and Therapeutics, 1994, 56(6 Pt 1): 659-67; and FDA label for quinidine at www.accessdata.fda.gov).

In general, combining drugs with cytochrome P450 inhibitors is not a satisfactory strategy for decreasing drug clearance. The inhibition of a CYP enzyme's activity can affect the metabolism and clearance of other drugs metabolized by that same enzyme. CYP inhibition can cause other drugs to accumulate in the body to toxic levels.

A potentially attractive strategy for improving a drug's metabolic properties is deuterium modification. In this approach, one attempts to slow the CYP-mediated metabolism of a drug or to reduce the formation of undesirable metabolites by replacing one or more hydrogen atoms with deuterium atoms. Deuterium is a safe, stable, non-radioactive isotope of hydrogen. Compared to hydrogen, deuterium forms stronger bonds with carbon. In select cases, the increased bond strength imparted by deuterium can positively impact the ADME properties of a drug, creating the potential for improved drug efficacy, safety, and/or tolerability. At the same time, because the size and shape of deuterium are essentially identical to those of hydrogen, replacement of hydrogen by deuterium would not be expected to affect the biochemical potency and selectivity of the drug as compared to the original chemical entity that contains only hydrogen.

Over the past 35 years, the effects of deuterium substitution on the rate of metabolism have been reported for a very small percentage of approved drugs (see, e.g., Blake, M I et al, J Pharm Sci, 1975, 64:367-91; Foster, A B, Adv Drug Res 1985, 14:1-40 ("Foster"); Kushner, D J et al, Can J Physiol Pharmacol 1999, 79-88; Fisher, M B et al, Curr Opin Drug Discov Devel, 2006, 9:101-09 ("Fisher")). The results have been variable and unpredictable. For some compounds deuteration caused decreased metabolic clearance in vivo. For others, there was no change in metabolism. Still others demonstrated increased metabolic clearance. The variability in deuterium effects has also led experts to question or dismiss deuterium modification as a viable drug design strategy for inhibiting adverse metabolism (see Foster at p. 35 and Fisher at p. 101).

The effects of deuterium modification on a drug's metabolic properties are not predictable even when deuterium atoms are incorporated at known sites of metabolism. Only by actually preparing and testing a deuterated drug can one determine if and how the rate of metabolism will differ from that of its non-deuterated counterpart. See, for example, Fukuto et al. (J. Med. Chem. 1991, 34, 2871-76). Many drugs have multiple sites where metabolism is possible. The site(s) where deuterium substitution is required and the extent of deuteration necessary to see an effect on metabolism, if any, will be different for each drug.

This invention relates to novel diaryl urea compounds, and pharmaceutically acceptable salts thereof. This invention also provides compositions comprising a compound of this invention and the use of such compositions in methods of treating diseases and conditions that are beneficially treated by administering an inhibitor of multiple kinases.

Sorafenib, also known as 4-[4-[3-[4-Chloro-3-(trifluoromethyl)phenyl]ureido]phenoxy]-N-methylpyridine-2-carboxamide, acts as a multikinase inhibitor, targeting serine/threonine and receptor tyrosine kinases in tumor cells and tumor vasculature.

Sorafenib is currently approved for the treatment of patients with renal cell carcinoma, advanced hepatocellular carcinoma as well as unresectable or metstatic hepatocellular carcinoma (liver cancer), and is in clinical trials for the treatment of various cancers including non-small cell lung, lung, breast, ovarian, fallopian tube, peritoneal cavity, pancreatic, bladder, metastatic prostate, thyroid, uterine, gastrointestinal stromal, metastatic melanoma, prostate adenocarcinoma, soft tissue sarcoma, mesothelioma, glioblastoma multiforme, acute myeloid leukemia, non-Hodgkin's lymphoma, multiple myeloma, glioblastoma, lymphoma, anaplastic astrocytoma, solid tumor, colorectal, squamous cell head and neck carcinoma, and oligodendroglioma. Sorafenib is also under clinical evaluation for pulmonary hypertension. (See http://clinicaltrials.gov/ct/search?term=sorafenib).

BAY 73-4506, a fluorinated version of sorafenib, also acts as a multikinase inhibitor which targets both the tumor and its vasculature. In particular, BAY 73-4506 is a potent inhibitor of Raf kinase, p38 kinase, platelet-derived growth factor receptor (PDGFR) kinase, and vascular endothelial growth factor receptor (VEGFR) kinases 2 and 3. Inhibition of these particular kinases has been associated with treatment and prevention of osteoporosis, inflammatory disorders, hyperproliferative disorders, and angiogenesis disorders, including cancer (Dumas, J et al., in PCT Publication WO 2005009961 A2; and Hedbom, S. et al., Journal of Clinical Oncology, 25, (Suppl. 18): Abs. 3593).

BAY 73-4506 is currently under clinical evaluation for treatment of renal cell carcinoma (ClinicalTrials.gov Web Site 2008, May 5), solid tumors (J Clin Oncol, 2008, 26(15, Suppl.): Abst 2558), hepatocellular carcinoma (ClinicalTrials.gov Web Site 2010, May 17) and metastatic colorectal cancer (ClinicalTrials.gov Web Site 2010, May 17). BAY 73-4506 is also under preclinical evaluation for multiple myeloma (Blood, 2008, 112(11): Abst 2766).

Sorafenib is metabolized primarily in the liver via oxidation or glucuronidation. The main circulating metabolite of sorafenib in plasma, the pyridine N-oxide (accounting for approximately 9-16% of circulating analytes at steady-state), shows in vitro potency similar to that of sorafenib. (See product label: http://www.fda.gov/cder/foi/label/2005/021923lbl.pdf).

Adverse events reported in at least 10% of patients treated with sorafenib include, but are not limited to, hypertension, fatigue, weight loss, rash, hand-foot skin reaction, alopecia, pruritis, diarrhea, nausea, vomiting, constipation, hemorrhage, sensory neuropathy, joint pain, and headache. (See product label: http://www.fda.gov/cder/foi/label/2005/021923lbl.pdf). The most common adverse events reported for patients treated with BAY 73-4506 in clinical trials for advanced solid tumors include hoarsenesss, grade 1-2 hypertension, hand-foot skin reaction, grade 1 mucositis and leukopenia (Hedbom, S. et al., Journal of Clinical Oncology, 25, (Suppl. 18): Abs. 3593).

Despite the beneficial activities of sorafenib and the potential benefits of BAY 73-4506, there is a continuing need for new compounds to treat the aforementioned diseases and conditions.

SUMMARY OF THE INVENTION

This invention relates to novel diaryl urea compounds, and pharmaceutically acceptable salts thereof. This invention also provides compositions comprising a compound of this invention and the use of such compositions in methods of treating diseases and conditions that are beneficially treated by administering an inhibitor of multiple kinases.

DETAILED DESCRIPTION OF THE INVENTION

The term "treat" means decrease, suppress, attenuate, diminish, arrest, or stabilize the development or progression of a disease (e.g., a disease or disorder delineated herein), lessen the severity of the disease or improve the symptoms associated with the disease.

"Disease" means any condition or disorder that damages or interferes with the normal function of a cell, tissue, or organ.

It will be recognized that some variation of natural isotopic abundance occurs in a synthesized compound depending upon the origin of chemical materials used in the synthesis. Thus, a preparation of BAY 73-4506 will inherently contain small amounts of deuterated isotopologues. The concentration of naturally abundant stable hydrogen and carbon isotopes, notwithstanding this variation, is small and immaterial as compared to the degree of stable isotopic substitution of compounds of this invention. See, for instance, Wada, E et al., Seikagaku, 1994, 66:15; Gannes, L Z et al., Comp Biochem Physiol Mol Integr Physiol, 1998, 119:725.

In the compounds of this invention any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Also unless otherwise stated, when a position is designated specifically as "D" or "deuterium", the position is understood to have deuterium at an abundance that is at least 3340 times greater than the natural abundance of deuterium, which is 0.015% (i.e., at least 50.1% incorporation of deuterium).

The term "isotopic enrichment factor" as used herein means the ratio between the isotopic abundance and the natural abundance of a specified isotope.

In other embodiments, a compound of this invention has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

The term "isotopologue" refers to a species in which the chemical structure differs from a specific compound of this invention only in the isotopic composition thereof.

The term "compound," when referring to a compound of this invention, refers to a collection of molecules having an identical chemical structure, except that there may be isotopic variation among the constituent atoms of the molecules. Thus, it will be clear to those of skill in the art that a compound represented by a particular chemical structure containing indicated deuterium atoms, will also contain lesser amounts of isotopologues having hydrogen atoms at one or more of the designated deuterium positions in that structure. The relative amount of such isotopologues in a compound of this invention will depend upon a number of factors including the isotopic purity of deuterated reagents used to make the compound and the efficiency of incorporation of deuterium in the various synthesis steps used to prepare the compound. However, as set forth above the relative amount of such isotopologues in toto will be less than 49.9% of the compound. In other embodiments, the relative amount of such isotopologues in toto will be less than 47.5%, less than 40%, less than 32.5%, less than 25%, less than 17.5%, less than 10%, less than 5%, less than 3%, less than 1%, or less than 0.5% of the compound.

The invention also provides salts of the compounds of the invention.

A salt of a compound of this invention is formed between an acid and a basic group of the compound, such as an amino functional group, or a base and an acidic group of the compound, such as a carboxyl functional group. According to another embodiment, the compound is a pharmaceutically acceptable acid addition salt.

The term "pharmaceutically acceptable," as used herein, refers to a component that is, within the scope of sound medical judgment, suitable for use in contact with the tissues of humans and other mammals without undue toxicity, irritation, allergic response and the like, and are commensurate with a reasonable benefit/risk ratio. A "pharmaceutically acceptable salt" means any non-toxic salt that, upon administration to a recipient, is capable of providing, either directly or indirectly, a compound of this invention. A "pharmaceutically acceptable counterion" is an ionic portion of a salt that is not toxic when released from the salt upon administration to a recipient.

Acids commonly employed to form pharmaceutically acceptable salts include inorganic acids such as hydrogen bisulfide, hydrochloric acid, hydrobromic acid, hydroiodic acid, sulfuric acid and phosphoric acid, as well as organic acids such as para-toluenesulfonic acid, salicylic acid, tartaric acid, bitartaric acid, ascorbic acid, maleic acid, besylic acid, fumaric acid, gluconic acid, glucuronic acid, formic acid, glutamic acid, methanesulfonic acid, ethanesulfonic acid, benzenesulfonic acid, lactic acid, oxalic acid, para-bromophenylsulfonic acid, carbonic acid, succinic acid, citric acid, benzoic acid and acetic acid, as well as related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephthalate, sulfonate, xylene sulfonate, phenylacetate, phenylpropionate, phenylbutyrate, citrate, lactate, β-hydroxybutyrate, glycolate, maleate, tartrate, methanesulfonate, propanesulfonate, naphthalene-1-sulfonate, naphthalene-2-sulfonate, mandelate and other salts. In one embodiment, pharmaceutically acceptable acid addition salts include those formed with mineral acids such as hydrochloric acid and hydrobromic acid, and especially those formed with organic acids such as maleic acid.

The compounds of the present invention (e.g., compounds of Formula I, IA or IB), may contain an asymmetric carbon atom, for example, as the result of deuterium substitution or otherwise. As such, compounds of this invention can exist as either individual enantiomers, or mixtures of the two enantiomers. Accordingly, a compound of the present invention may exist as either a racemic mixture or a scalemic mixture, or as individual respective stereoisomers that are substantially free from another possible stereoisomer. The term "substantially free of other stereoisomers" as used herein means less than 25% of other stereoisomers, preferably less than 10% of other stereoisomers, more preferably less than 5% of other stereoisomers and most preferably less than 2% of other stereoisomers are present. Methods of obtaining or synthesizing an individual enantiomer for a given compound are known in the art and may be applied as practicable to final compounds or to starting material or intermediates.

Unless otherwise indicated, when a disclosed compound is named or depicted by a structure without specifying the stereochemistry and has one or more chiral centers, it is understood to represent all possible stereoisomers of the compound.

The term "stable compounds," as used herein, refers to compounds which possess stability sufficient to allow for their manufacture and which maintain the integrity of the compound for a sufficient period of time to be useful for the purposes detailed herein (e.g., formulation into therapeutic products, intermediates for use in production of therapeutic compounds, isolatable or storable intermediate compounds, treating a disease or condition responsive to therapeutic agents).

"D" and "d" both refer to deuterium. "Stereoisomer" refers to both enantiomers and diastereomers. "Tert" and "t-" each refer to tertiary. "US" refers to the United States of America.

Throughout this specification, a variable may be referred to generally (e.g., "each R") or may be referred to specifically (e.g., $R^1$, $R^2$, $R^3$, etc.). Unless otherwise indicated, when a variable is referred to generally, it is meant to include all specific embodiments of that particular variable.

Therapeutic Compounds

The present invention provides a compound of Formula I:

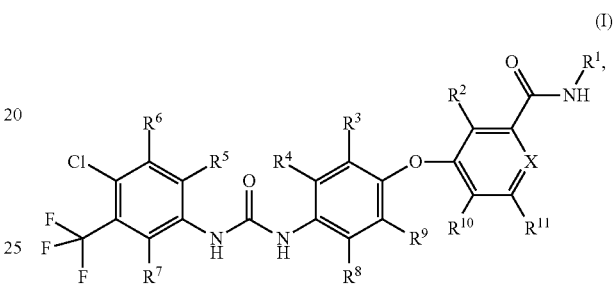

or a pharmaceutically acceptable salt thereof, wherein:
X is selected from N and $N^+$—$O^-$;
$R^1$ is selected from $CH_3$, $CH_2D$, $CHD_2$ and $CD_3$;
each of $R^2$, $R^3$, $R^4$, $R^5$, $R^6$, $R^7$, $R^8$, $R^9$, $R^{10}$ and $R^{11}$ is independently selected from F, H and D; and
at least one R group comprises a deuterium atom; and
at least one of $R^2$, $R^3$, $R^4$, $R^5$, $R^6$, $R^7$, $R^8$, $R^9$, $R^{10}$ and $R^{11}$ comprises a fluorine atom.

In one embodiment of a compound of Formula I, X is N and $R^1$ is $CH_3$ or $CD_3$. In one aspect of this embodiment, $R^2$, $R^{10}$ and $R^{11}$ are independently selected from F and H. In an alternate aspect of this embodiment $R^2$, $R^{10}$ and $R^{11}$ are independently selected from F and D. In another aspect of this embodiment, $R^3$, $R^4$, $R^8$ and $R^9$ are independently selected from F and H. In yet another aspect of this embodiment, $R^3$, $R^4$, $R^8$ and $R^9$ are independently selected from F and D. In still another aspect of this embodiment, $R^5$, $R^6$ and $R^7$ are independently selected from F and H. In yet another aspect of this embodiment $R^5$, $R^6$ and $R^7$ are independently selected from F and D.

In still other aspects of the embodiment of a compound of Formula I, wherein X is N, and $R^1$ is $CH_3$ or $CD_3$:
a) $R^2$, $R^{10}$ and $R^{11}$ are independently selected from F and H; and $R^3$, $R^4$, $R^8$ and $R^9$ are independently selected from F and H;
b) $R^2$, $R^{10}$ and $R^{11}$ are independently selected from F and D; and $R^3$, $R^4$, $R^8$ and $R^9$ are independently selected from F and H;
c) $R^2$, $R^{10}$ and $R^{11}$ are independently selected from F and H; and $R^3$, $R^4$, $R^8$ and $R^9$ are independently selected from F and D;
d) $R^2$, $R^{10}$ and $R^{11}$ are independently selected from F and D; and $R^3$, $R^4$, $R^8$ and $R^9$ are independently selected from F and D;
e) $R^2$, $R^{10}$ and $R^{11}$ are independently selected from F and H; and $R^5$, $R^6$ and $R^7$ are independently selected from F and H;
f) $R^2$, $R^{10}$ and $R^{11}$ are independently selected from F and D; and $R^5$, $R^6$ and $R^7$ are independently selected from F and H;

g) $R^2$, $R^{10}$ and $R^{11}$ are independently selected from F and H; and $R^5$, $R^6$ and $R^7$ are independently selected from F and D;

h) $R^2$, $R^{10}$ and $R^{11}$ are independently selected from F and D; and $R^5$, $R^6$ and $R^7$ are independently selected from F and D;

i) $R^2$, $R^{10}$ and $R^{11}$ are independently selected from F and H; $R^3$, $R^4$, $R^8$ and $R^9$ are independently selected from F and H; and $R^5$, $R^6$ and $R^7$ are independently selected from F and H;

j) $R^2$, $R^{10}$ and $R^{11}$ are independently selected from F and D; $R^3$, $R^4$, $R^8$ and $R^9$ are independently selected from F and H; and $R^5$, $R^6$ and $R^7$ are independently selected from F and H;

k) $R^2$, $R^{10}$ and $R^{11}$ are independently selected from F and H; $R^3$, $R^4$, $R^8$ and $R^9$ are independently selected from F and D; and $R^5$, $R^6$ and $R^7$ are independently selected from F and H;

l) $R^2$, $R^{10}$ and $R^{11}$ are independently selected from F and H; $R^3$, $R^4$, $R^8$ and $R^9$ are independently selected from F and H; and $R^5$, $R^6$ and $R^7$ are independently selected from F and D;

m) $R^2$, $R^{10}$ and $R^{11}$ are independently selected from F and D; $R^3$, $R^4$, $R^8$ and $R^9$ are independently selected from F and D; and $R^5$, $R^6$ and $R^7$ are independently selected from F and H;

n) $R^2$, $R^{10}$ and $R^{11}$ are independently selected from F and H; $R^3$, $R^4$, $R^8$ and $R^9$ are independently selected from F and D; and $R^5$, $R^6$ and $R^7$ are independently selected from F and D;

o) $R^2$, $R^{10}$ and $R^{11}$ are independently selected from F and D; $R^3$, $R^4$, $R^8$ and $R^9$ are independently selected from F and H; and $R^5$, $R^6$ and $R^7$ are independently selected from F and D; and p) $R^2$, $R^{10}$ and $R^{11}$ are independently selected from F and D; $R^3$, $R^4$, $R^8$ and $R^9$ are independently selected from F and D; and $R^5$, $R^6$ and $R^7$ are independently selected from F and D.

Another embodiment relates to a compound of Formula I, wherein X is N, $R^1$ is $CH_3$ or $CD_3$; one or two of $R^2$, $R^3$, $R^4$, $R^5$, $R^6$, $R^7$, $R^8$, $R^9$, $R^{10}$ and $R^{11}$ is fluorine; and the others of $R^2$, $R^3$, $R^4$, $R^5$, $R^6$, $R^7$, $R^8$, $R^9$, $R^{10}$ and $R^{11}$ are selected from D and H. In one aspect of this embodiment, only one of $R^2$, $R^3$, $R^4$, $R^5$, $R^6$, $R^7$, $R^8$, $R^9$, $R^{10}$ and $R^{11}$ is fluorine (i.e., only $R^2$ is fluorine, only $R^3$ is fluorine, only $R^4$ is fluorine, only $R^5$ is fluorine, only $R^6$ is fluorine, only $R^7$ is fluorine, only $R^8$ is fluorine, only $R^9$ is fluorine, only $R^{10}$ is fluorine, or only $R^{11}$ is fluorine) and the others of $R^2$, $R^3$, $R^4$, $R^5$, $R^6$ $R^7$, $R^8$, $R^9$, $R^{10}$ and $R^{11}$ are selected from D and H. In another aspect of this embodiment, $R^2$, $R^{10}$ and $R^{11}$ are simultaneously D or H. In another aspect of this embodiment $R^3$, $R^4$, $R^8$ and $R^9$ are simultaneously D or H. In still another aspect of this embodiment $R^5$, $R^6$ and $R^7$ are simultaneously D or H. In yet another aspect of this embodiment, any of $R^2$, $R^{10}$ and $R^{11}$ that are not fluorine are the same (e.g., if $R^2$ is fluorine, then $R^{10}$ and $R^{11}$ are both hydrogen or both deuterium); any of $R^3$, $R^4$, $R^8$ and $R^9$ that are not fluorine are the same; and any of $R^5$, $R^6$ and $R^7$ that are not fluorine are the same.

In another embodiment of Formula I, X is N; $R^1$ is $CH_3$ or $CD_3$; $R^4$ is fluorine; and each of $R^2$, $R^3$, $R^5$, $R^6$, $R^7$, $R^8$, $R^9$, $R^{10}$ and $R^{11}$ is independently selected from D and H, said compound having the structural formula depicted in Formula IA:

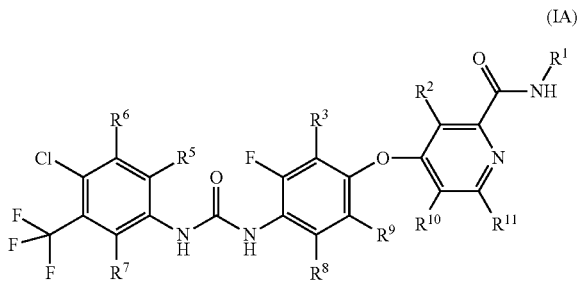

(IA)

or a pharmaceutically acceptable salt thereof.

In one aspect of Formula IA, $R^2$, $R^{10}$ and $R^{11}$ are simultaneously D or H. In another aspect of Formula IA, $R^3$, $R^8$ and $R^9$ are simultaneously D or H. In still another aspect of Formula IA, $R^5$, $R^6$ and $R^7$ are simultaneously D or H. In a more specific aspect of Formula IA, $R^2$, $R^{10}$ and $R^{11}$ are simultaneously D or H; $R^3$, $R^8$ and $R^9$ are simultaneously D or H; and $R^5$, $R^6$ and $R^7$ are simultaneously D or H.

Examples of specific compounds of Formula IA:

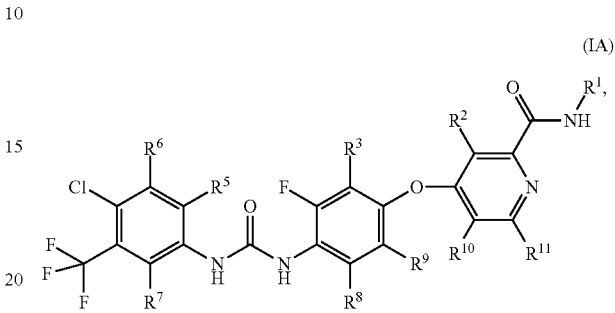

(IA)

are set forth in Table 1, below:

TABLE 1

Specific Examples of Formula IA

| Compound | $R^1$ | $R^2$ | $R^3$ | $R^5$ | $R^6$ | $R^7$ | $R^8$ | $R^9$ | $R^{10}$ | $R^{11}$ |
|---|---|---|---|---|---|---|---|---|---|---|
| 100 | $CH_3$ | D | D | D | D | D | D | D | D | D |
| 101 | $CH_3$ | H | D | D | D | D | D | D | H | H |
| 102 | $CH_3$ | D | H | D | D | D | H | H | D | D |
| 103 | $CH_3$ | D | D | H | H | H | D | D | D | D |
| 104 | $CH_3$ | H | H | D | D | D | H | H | H | H |
| 105 | $CH_3$ | H | D | H | H | H | D | H | H | H |
| 106 | $CH_3$ | D | H | H | H | H | H | H | D | D |
| 107 | $CD_3$ | D | D | D | D | D | D | D | D | D |
| 108 | $CD_3$ | H | D | D | D | D | D | D | H | H |
| 109 | $CD_3$ | D | H | D | D | D | H | H | D | D |
| 110 | $CD_3$ | D | D | H | H | H | D | D | D | D |
| 111 | $CD_3$ | H | H | D | D | D | H | H | H | H |
| 112 | $CD_3$ | H | D | H | H | H | D | H | H | H |
| 113 | $CD_3$ | D | H | H | H | H | H | H | D | D |
| 114 | $CD_3$ | H | H | H | H | H | H | H | H | H | or a pharmaceutically acceptable salt of any of the foregoing.

In one embodiment of a compound of Formula I, X is $N^+$—$O^-$ and $R^1$ is $CH_3$ or $CD_3$. In one aspect of this embodiment, $R^2$, $R^{10}$ and $R^{11}$ are independently selected from F and H. In an alternate aspect of this embodiment $R^2$, $R^{10}$ and $R^{11}$ are independently selected from F and D. In another aspect of this embodiment, $R^3$, $R^4$, $R^8$ and $R^9$ are independently selected from F and H. In yet another aspect of this embodiment, $R^3$, $R^4$, $R^8$ and $R^9$ are independently selected from F and D. In still another aspect of this embodiment, $R^5$, $R^6$ and $R^7$ are independently selected from F and H. In yet another aspect of this embodiment $R^5$, $R^6$ and $R^7$ are independently selected from F and D.

In still other aspects of the embodiment of a compound of Formula I, wherein X is $N^+$—$O^-$, and $R^1$ is $CH_3$ or $CD_3$:

a) $R^2$, $R^{10}$ and $R^{11}$ are independently selected from F and H; and $R^3$, $R^4$, $R^8$ and $R^9$ are independently selected from F and H;

b) $R^2$, $R^{10}$ and $R^{11}$ are independently selected from F and D; and $R^3$, $R^4$, $R^8$ and $R^9$ are independently selected from F and H;

c) $R^2$, $R^{10}$ and $R^{11}$ are independently selected from F and H; and $R^3$, $R^4$, $R^8$ and $R^9$ are independently selected from F and D;

d) $R^2$, $R^{10}$ and $R^{11}$ are independently selected from F and D; and $R^3$, $R^4$, $R^8$ and $R^9$ are independently selected from F and D;

e) $R^2$, $R^{10}$ and $R^{11}$ are independently selected from F and H; and $R^5$, $R^6$ and $R^7$ are independently selected from F and H;

f) $R^2$, $R^{10}$ and $R^{11}$ are independently selected from F and D; and $R^5$, $R^6$ and $R^7$ are independently selected from F and H;

g) $R^2$, $R^{10}$ and $R^{11}$ are independently selected from F and H; and $R^5$, $R^6$ and $R^7$ are independently selected from F and D;

h) $R^2$, $R^{10}$ and $R^{11}$ are independently selected from F and D; and $R^5$, $R^6$ and $R^7$ are independently selected from F and D;

i) $R^2$, $R^{10}$ and $R^{11}$ are independently selected from F and H; $R^3$, $R^4$, $R^8$ and $R^9$ are independently selected from F and H; and $R^5$, $R^6$ and $R^7$ are independently selected from F and H;

j) $R^2$, $R^{10}$ and $R^{11}$ are independently selected from F and D; $R^3$, $R^4$, $R^8$ and $R^9$ are independently selected from F and H; and $R^5$, $R^6$ and $R^7$ are independently selected from F and H;

k) $R^2$, $R^{10}$ and $R^{11}$ are independently selected from F and H; $R^3$, $R^4$, $R^8$ and $R^9$ are independently selected from F and D; and $R^5$, $R^6$ and $R^7$ are independently selected from F and H;

l) $R^2$, $R^{10}$ and $R^{11}$ are independently selected from F and H; $R^3$, $R^4$, $R^8$ and $R^9$ are independently selected from F and H; and $R^5$, $R^6$ and $R^7$ are independently selected from F and D;

m) $R^2$, $R^{10}$ and $R^{11}$ are independently selected from F and D; $R^3$, $R^4$, $R^8$ and $R^9$ are independently selected from F and D; and $R^5$, $R^6$ and $R^7$ are independently selected from F and H;

n) $R^2$, $R^{10}$ and $R^{11}$ are independently selected from F and H; $R^3$, $R^4$, $R^8$ and $R^9$ are independently selected from F and D; and $R^5$, $R^6$ and $R^7$ are independently selected from F and D;

o) $R^2$, $R^{10}$ and $R^{11}$ are independently selected from F and D; $R^3$, $R^4$, $R^8$ and $R^9$ are independently selected from F and H; and $R^5$, $R^6$ and $R^7$ are independently selected from F and D; and p) $R^2$, $R^{10}$ and $R^{11}$ are independently selected from F and D; $R^3$, $R^4$, $R^8$ and $R^9$ are independently selected from F and D; and $R^5$, $R^6$ and $R^7$ are independently selected from F and D.

Another embodiment relates to a compound of Formula I, wherein X is $N^+$—$O^-$, $R^1$ is $CH_3$ or $CD_3$; one or two of $R^2$, $R^3$, $R^4$, $R^5$, $R^6$, $R^7$, $R^8$, $R^9$, $R^{10}$ and $R^{11}$ is fluorine; and the others of $R^2$, $R^3$, $R^4$, $R^5$, $R^6$, $R^7$, $R^8$, $R^9$, $R^{10}$ and $R^{11}$ are selected from D and H. In one aspect of this embodiment, only one of $R^2$, $R^3$, $R^4$, $R^5$, $R^6$, $R^7$, $R^8$, $R^9$, $R^{10}$ and $R^{11}$ is fluorine (i.e., only $R^2$ is fluorine, only $R^3$ is fluorine, only $R^4$ is fluorine, only $R^5$ is fluorine, only $R^6$ is fluorine, only $R^7$ is fluorine, only $R^8$ is fluorine, only $R^9$ is fluorine, only $R^{10}$ is fluorine, or only $R^{11}$ is fluorine) and the others of $R^2$, $R^3$, $R^4$, $R^5$, $R^6$, $R^7$, $R^8$, $R^9$, $R^{10}$ and $R^{11}$ are selected from D and H. In another aspect of this embodiment, $R^2$, $R^{10}$ and $R^{11}$ are simultaneously D or H. In another aspect of this embodiment $R^3$, $R^4$, $R^8$ and $R^9$ are simultaneously D or H. In still another aspect of this embodiment $R^5$, $R^6$ and $R^7$ are simultaneously D or H. In yet another aspect of this embodiment, any of $R^2$, $R^{10}$ and $R^{11}$ that are not fluorine are the same (e.g., if $R^2$ is fluorine, then $R^{10}$ and $R^{11}$ are both hydrogen or both deuterium); any of $R^3$, $R^4$, $R^8$ and $R^9$ that are not fluorine are the same; and any of $R^5$, $R^6$ and $R^7$ that are not fluorine are the same.

In another embodiment of Formula I, X is $N^+$—$O^-$; $R^1$ is $CH_3$ or $CD_3$; $R^4$ is flourine; and each of $R^2$, $R^3$, $R^5$, $R^6$, $R^7$, $R^8$, $R^9$, $R^{10}$ and $R^{11}$ is independently selected from D and H, said compound having the structural formula depicted in Formula IB:

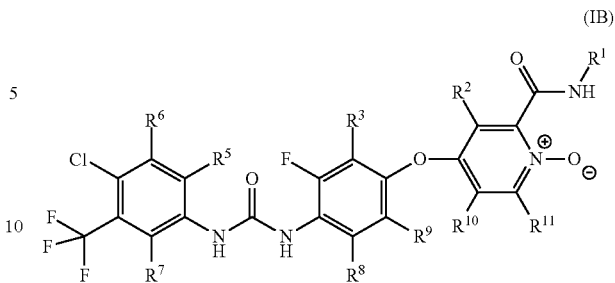

(IB)

or a pharmaceutically acceptable salt thereof.

In one aspect of Formula IB, $R^2$, $R^{10}$ and $R^{11}$ are simultaneously D or H. In another aspect of Formula IB, $R^3$, $R^8$ and $R^9$ are simultaneously D or H. In still another aspect of Formula IB, $R^5$, $R^6$ and $R^7$ are simultaneously D or H. In a more specific aspect of Formula IB, $R^2$, $R^{10}$ and $R^{11}$ are simultaneously D or H; $R^3$, $R^8$ and $R^9$ are simultaneously D or H; and $R^5$, $R^6$ and $R^7$ are simultaneously D or H.

In another set of embodiments, any atom not designated as deuterium in any of the embodiments set forth above is present at its natural isotopic abundance.

The synthesis of compounds of Formula I can be readily achieved by synthetic chemists of ordinary skill by reference to the Exemplary Synthesis and Examples disclosed herein. Relevant procedures analogous to those of use for the preparation of compounds of Formula I and intermediates thereof are disclosed, for instance in PCT publications WO 2005009961, WO 2000041698 and WO 2000042012; and in Sorbera, L A et al., Drugs Fut 2002, 27(12):1141; and Bankston, D et al., Org Process Res Dev 2002, 6(6): 777.

Such methods can be carried out utilizing corresponding deuterated and optionally, other isotope-containing reagents and/or intermediates to synthesize the compounds delineated herein, or invoking standard synthetic protocols known in the art for introducing isotopic atoms to a chemical structure.

Exemplary Synthesis

Convenient methods for synthesizing compounds of Formula I are depicted in Schemes 1-4.

Scheme 1. Synthesis of Compounds of Formula I.

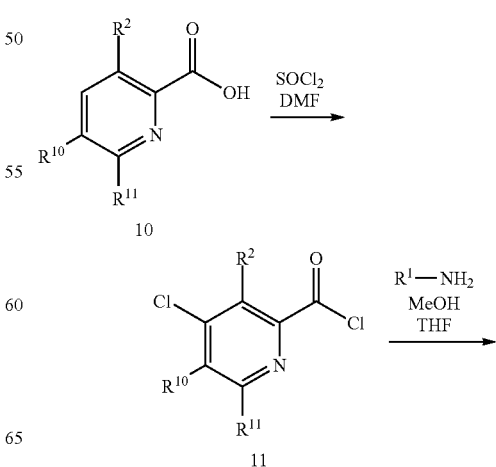

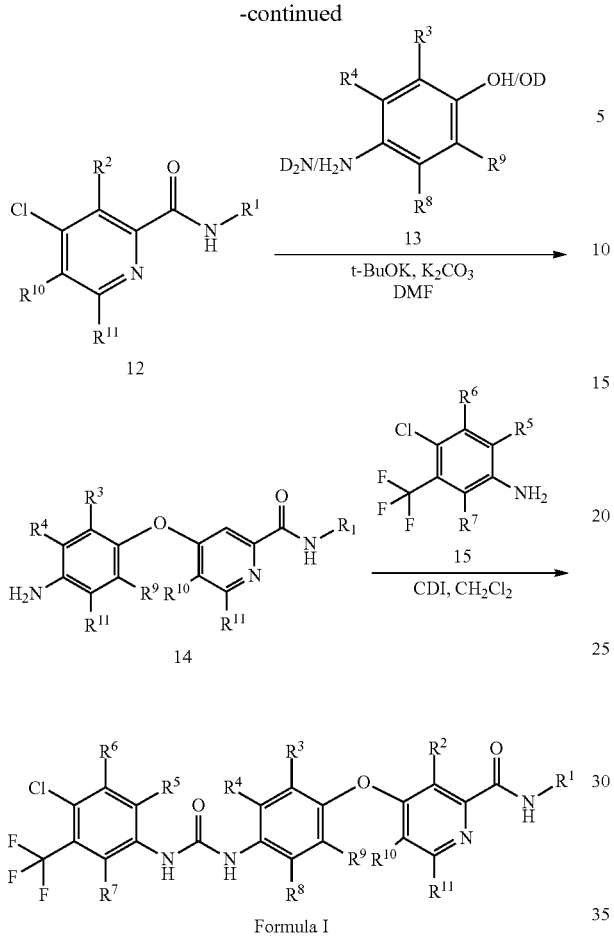

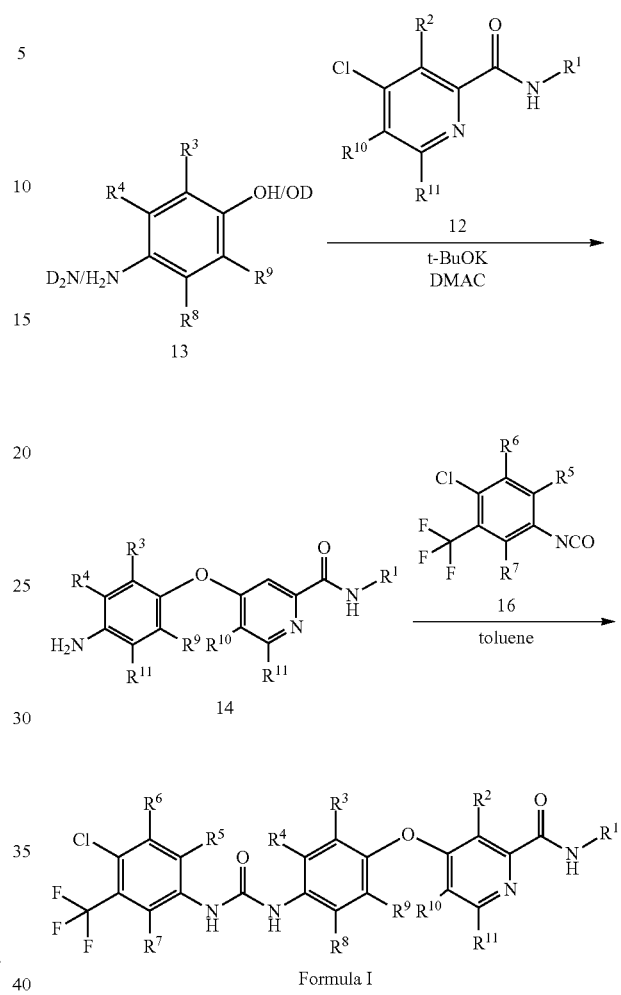

Scheme 1b. Alternative Synthesis of Compounds of Formula I.

A convenient method for synthesizing compounds of Formula I is depicted in Scheme 1, above, where the use of appropriately deuterated and/or fluorinated intermediates and reagents results in the production of various compounds of Formula I. The slashes in Scheme 1 (e.g. OH/OD in 13) indicate that reagents containing either of the indicated moieties may be used depending upon the deuteration desired. Thus, appropriately substituted carboxylic acid 10 is converted to the acid chloride 11 under conventional conditions. Treatment of 11 with a primary amine provides amide 12, which can subsequently be converted to diphenyl ether 14 using compound 13 in the presence of base. Coupling of 14 to 15 using CDI (1,1'-carbonyldiimidazole) then provides a compound of Formula I.

In one example, commercially available picolinic-d$_4$ acid is used as acid 10 to afford compounds of Formula I wherein $R^2$, $R^{10}$ and $R^{11}$ are deuterium. Other commercially available compounds which may used as intermediate 10 in Scheme 1 include, but are not limited to, 3,6-difluoropyridine-2-carboxylic acid; 5,6-difluoropyridine-2-carboxylic acid; 3,5-difluoropicolinic acid; 3-fluoropicolinic acid; 5-fluoro-2-picolinic acid; 6-fluoropicolinic acid; and picolinic acid.

In another example, commercially-available 4-chloro-3-(trifluoromethyl)aniline is used as 15 to afford compounds of Formula I wherein $R^5$, $R^6$, and $R^7$ are hydrogen.

The use of commercially available methyl-d$_3$ amine in Scheme 1, in the conversion of 11 to 12, produces compounds of Formula I wherein $R^1$ is CD$_3$.

An alternative method for preparing compounds of Formula I is depicted in Scheme 1b, above. Appropriately substituted 13 is treated with potassium tert-butoxide in N,N-dimethylacetamide (DMAC), followed by addition of appropriately substituted amide 12 to afford diphenyl ether 14. Treatment of 14 with appropriately substituted isocyanate 16 in toluene provides compounds of Formula I.

In one example, commercially available 4-aminophenol-d$_7$ can be used as reagent 13 in Schemes 1 and 1b to produce compounds of Formula I wherein $R^3$, $R^4$, $R^8$, and $R^9$ are deuterium. In yet another example, commercially available 4-amino-3-fluorophenol is used as reagent 13 to afford compounds of Formula I wherein $R^4$ is fluorine.

Other commercially available compounds which may be of use as reagent 13 in Schemes 1 and 1b include, but are not limited to, 4-aminophenol; 4-amino-2,6-difluorophenol; 4-amino-2,3-difluoro-phenol; 4-amino-2,3,5-trifluoro-phenol; 4-amino-3,5-difluoro-phenol; 4-amino-2,3,6-trifluorophenol; 4-amino-2,5-difluorophenol; and 4-amino-3-fluorophenol.

In yet another example, commercially available 4-chloro-3-(trifluoromethyl)phenyl isocyanate may be used as reagent 16 to afford compounds of Formula I wherein $R^5$, $R^6$ and $R^7$ are hydrogen.

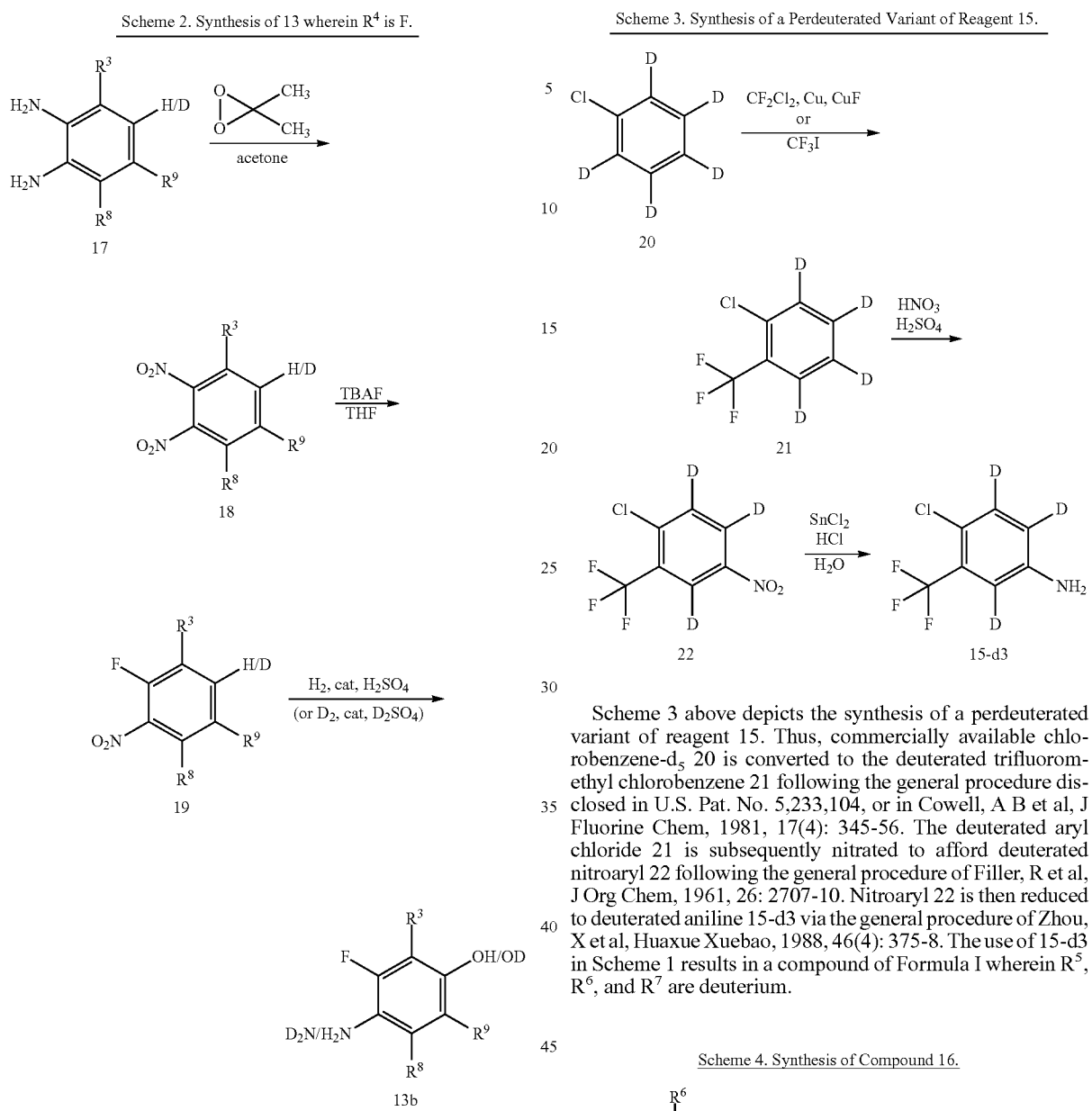

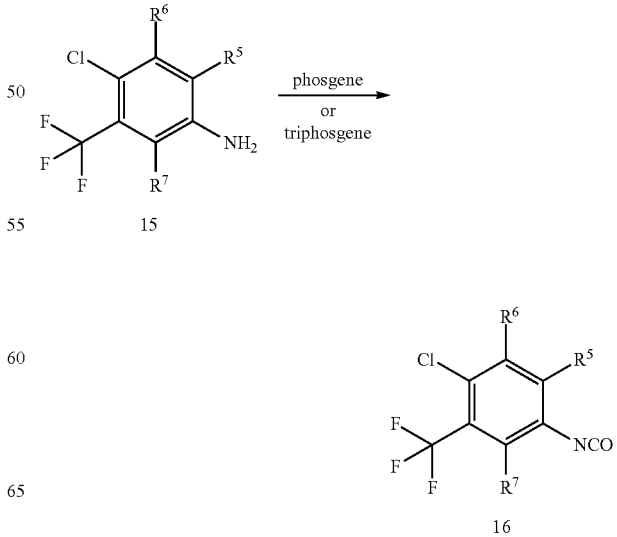

Scheme 3 above depicts the synthesis of a perdeuterated variant of reagent 15. Thus, commercially available chlorobenzene-d$_5$ 20 is converted to the deuterated trifluoromethyl chlorobenzene 21 following the general procedure disclosed in U.S. Pat. No. 5,233,104, or in Cowell, A B et al, J Fluorine Chem, 1981, 17(4): 345-56. The deuterated aryl chloride 21 is subsequently nitrated to afford deuterated nitroaryl 22 following the general procedure of Filler, R et al, J Org Chem, 1961, 26: 2707-10. Nitroaryl 22 is then reduced to deuterated aniline 15-d3 via the general procedure of Zhou, X et al, Huaxue Xuebao, 1988, 46(4): 375-8. The use of 15-d3 in Scheme 1 results in a compound of Formula I wherein $R^5$, $R^6$, and $R^7$ are deuterium.

Scheme 2 above depicts the synthesis of a variant of 13 wherein $R^4$ is fluorine. Appropriately substituted diamine 17 is oxidized with dimethyldioxirane according to the general procedures of Murray, R W, et al J Org Chem 1989, 54(24): 5783-5788 to afford dinitrophenyl 18. Treatment of 18 with tetrabutylammonium fluoride (TBAF) according to the general method of Clark, J H, et al, Tet Lett 1985, 26(18):2233-2236 provides fluoronitrobenzene 19. Treatment of 19 with hydrogen and H$_2$SO$_4$ in the presence of a catalyst such as palladium or platinum, according to the general methods found in patent applications JP 04182456, CN 101274898, and EP 490218, affords reagent 13b. If desired, deuterium gas and D$_2$SO$_4$ may be used in the conversion of 19 to 13b.

In one example, commercially available 1,2-benzene-d$_4$-diamine is used as diamine 17 in Scheme 2 to provide 13b wherein $R^3$, $R^8$ and $R^9$ are deuterium and $R^4$ is fluorine. Use of 13b in Schemes 1 or 1b provides compounds of Formula I wherein $R^3$, $R^8$ and $R^9$ are deuterium and $R^4$ is fluorine.

Scheme 4 above depicts the preparation of isocyanate 16. Appropriately substituted amine 15 is treated with either phosgene or triphosgene according to the general methods of Payen, O.; et al. J. Med. Chem. 2008, 51(6), 1791-1799, or of Xu, Z et al. J. Ind. Chem. Soc. 2002, 79(12), 962-963, to afford isocyanate 16.

The use of two or more deuterated and/or fluorinated intermediates or reagents described in Schemes 1 and 1b above produce additional compounds of Formula I containing additional sites of deuteration and/or fluorination.

N-oxide forms of a compound of Formula I (e.g., compounds depicted in Formula IB) are synthesized by oxidizing the pyridine ring nitrogen using an oxidant such as meta-chloroperoxybenzoic acid (m-CPBA) or hydrogen peroxide.

The specific approaches and compounds shown above are not intended to be limiting. The chemical structures in the schemes herein depict variables that are hereby defined commensurately with chemical group definitions (moieties, atoms, etc.) of the corresponding position in the compound formulae herein, whether identified by the same variable name (i.e., $R^1$, $R^2$, $R^3$, etc.) or not. The suitability of a chemical group in a compound structure for use in the synthesis of another compound is within the knowledge of one of ordinary skill in the art.

Additional methods of synthesizing compounds of Formula I and their synthetic precursors, including those within routes not explicitly shown in schemes herein, are within the means of chemists of ordinary skill in the art. Synthetic chemistry transformations and protecting group methodologies (protection and deprotection) useful in synthesizing the applicable compounds are known in the art and include, for example, those described in Larock R, *Comprehensive Organic Transformations*, VCH Publishers (1989); Greene, T W et al., *Protective Groups in Organic Synthesis*, $3^{rd}$ Ed., John Wiley and Sons (1999); Fieser, L et al., *Fieser and Fieser's Reagents for Organic Synthesis*, John Wiley and Sons (1994); and Paquette, L, ed., *Encyclopedia of Reagents for Organic Synthesis*, John Wiley and Sons (1995) and subsequent editions thereof Combinations of substituents and variables envisioned by this invention are only those that result in the formation of stable compounds.

Compositions

The invention also provides pyrogen-free pharmaceutical compositions comprising an effective amount of a compound of Formula I, IA or IB, or a pharmaceutically acceptable salt of said compound; and a pharmaceutically acceptable carrier. The carrier(s) are "acceptable" in the sense of being compatible with the other ingredients of the formulation and, in the case of a pharmaceutically acceptable carrier, not deleterious to the recipient thereof in an amount used in the medicament.

Pharmaceutically acceptable carriers, adjuvants and vehicles that may be used in the pharmaceutical compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

If required, the solubility and bioavailability of the compounds of the present invention in pharmaceutical compositions may be enhanced by methods well-known in the art. One method includes the use of lipid excipients in the formulation. See "Oral Lipid-Based Formulations: Enhancing the Bioavailability of Poorly Water-Soluble Drugs (Drugs and the Pharmaceutical Sciences)," David J. Hauss, ed. Informa Healthcare, 2007; and "Role of Lipid Excipients in Modifying Oral and Parenteral Drug Delivery: Basic Principles and Biological Examples," Kishor M. Wasan, ed. Wiley-Interscience, 2006.

Another known method of enhancing bioavailability is the use of an amorphous form of a compound of this invention optionally formulated with a poloxamer, such as LUTROL™ and PLURONIC™ (BASF Corporation), or block copolymers of ethylene oxide and propylene oxide. See U.S. Pat. No. 7,014,866; and United States patent publications 20060094744 and 20060079502.

The pharmaceutical compositions of the invention include those suitable for oral, rectal, nasal, topical (including buccal and sublingual), vaginal or parenteral (including subcutaneous, intramuscular, intravenous and intradermal) administration. In certain embodiments, the compound of the formulae herein is administered transdermally (e.g., using a transdermal patch or iontophoretic techniques). Other formulations may conveniently be presented in unit dosage form, e.g., tablets, sustained release capsules, and in liposomes, and may be prepared by any methods well known in the art of pharmacy. See, for example, Remington: The Science and Practice of Pharmacy, Lippincott Williams & Wilkins, Baltimore, Md. (20th ed. 2000).

Such preparative methods include the step of bringing into association with the molecule to be administered ingredients such as the carrier that constitutes one or more accessory ingredients. In general, the compositions are prepared by uniformly and intimately bringing into association the active ingredients with liquid carriers, liposomes or finely divided solid carriers, or both, and then, if necessary, shaping the product.

In certain embodiments, the compound is administered orally. Compositions of the present invention suitable for oral administration may be presented as discrete units such as capsules, sachets, or tablets each containing a predetermined amount of the active ingredient; a powder or granules; a solution or a suspension in an aqueous liquid or a non-aqueous liquid; an oil-in-water liquid emulsion; a water-in-oil liquid emulsion; packed in liposomes; or as a bolus, etc. Soft gelatin capsules can be useful for containing such suspensions, which may beneficially increase the rate of compound absorption.

In the case of tablets for oral use, carriers that are commonly used include lactose and corn starch. Lubricating agents, such as magnesium stearate, are also typically added. For oral administration in a capsule form, useful diluents include lactose and dried cornstarch. When aqueous suspensions are administered orally, the active ingredient is combined with emulsifying and suspending agents. If desired, certain sweetening and/or flavoring and/or coloring agents may be added.

Compositions suitable for oral administration include lozenges comprising the ingredients in a flavored basis, usually sucrose and acacia or tragacanth; and pastilles comprising the active ingredient in an inert basis such as gelatin and glycerin, or sucrose and acacia.

Compositions suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze dried (lyophilized) condition requiring only the addition of the sterile liquid carrier, for example water for injections, immediately prior to use. Extemporaneous injection solutions and suspensions may be prepared from sterile powders, granules and tablets.

Such injection solutions may be in the form, for example, of a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally-acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant.

The pharmaceutical compositions of this invention may be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art. See, e.g.: Rabinowitz J D and Zaffaroni A C, U.S. Pat. No. 6,803,031, assigned to Alexza Molecular Delivery Corporation.

Topical administration of the pharmaceutical compositions of this invention is especially useful when the desired treatment involves areas or organs readily accessible by topical application. For topical application topically to the skin, the pharmaceutical composition should be formulated with a suitable ointment containing the active components suspended or dissolved in a carrier. Carriers for topical administration of the compounds of this invention include, but are not limited to, mineral oil, liquid petroleum, white petroleum, propylene glycol, polyoxyethylene polyoxypropylene compound, emulsifying wax, and water. Alternatively, the pharmaceutical composition can be formulated with a suitable lotion or cream containing the active compound suspended or dissolved in a carrier. Suitable carriers include, but are not limited to, mineral oil, sorbitan monostearate, polysorbate 60, cetyl esters wax, cetearyl alcohol, 2-octyldodecanol, benzyl alcohol, and water. The pharmaceutical compositions of this invention may also be topically applied to the lower intestinal tract by rectal suppository formulation or in a suitable enema formulation. Topically-transdermal patches and iontophoretic administration are also included in this invention.

Application of the subject therapeutics may be local, so as to be administered at the site of interest. Various techniques can be used for providing the subject compositions at the site of interest, such as injection, use of catheters, trocars, projectiles, pluronic gel, stents, sustained drug release polymers or other device which provides for internal access.

Thus, according to yet another embodiment, the compounds of this invention may be incorporated into compositions for coating an implantable medical device, such as prostheses, artificial valves, vascular grafts, stents, or catheters. Suitable coatings and the general preparation of coated implantable devices are known in the art and are exemplified in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccharides, polyethylene glycol, phospholipids or combinations thereof to impart controlled release characteristics in the composition. Coatings for invasive devices are to be included within the definition of pharmaceutically acceptable carrier, adjuvant or vehicle, as those terms are used herein.

According to another embodiment, the invention provides a method of coating an implantable medical device comprising the step of contacting said device with the coating composition described above. It will be obvious to those skilled in the art that the coating of the device will occur prior to implantation into a mammal.

According to another embodiment, the invention provides a method of impregnating an implantable drug release device comprising the step of contacting said drug release device with a compound or composition of this invention. Implantable drug release devices include, but are not limited to, biodegradable polymer capsules or bullets, non-degradable, diffusible polymer capsules and biodegradable polymer wafers.

According to another embodiment, the invention provides an implantable medical device coated with a compound or a composition comprising a compound of this invention, such that said compound is therapeutically active.

According to another embodiment, the invention provides an implantable drug release device impregnated with or containing a compound or a composition comprising a compound of this invention, such that said compound is released from said device and is therapeutically active.

Where an organ or tissue is accessible because of removal from the patient, such organ or tissue may be bathed in a medium containing a composition of this invention, a composition of this invention may be painted onto the organ, or a composition of this invention may be applied in any other convenient way.

In another embodiment, a composition of this invention further comprises a second therapeutic agent. The second therapeutic agent may be selected from any compound or therapeutic agent known to have or that demonstrates advantageous properties when administered with a compound having the same mechanism of action as sorafenib or BAY 73-4506. Such agents include those indicated as being useful in combination with sorafenib or BAY 73-4506, including but not limited to, those described in WO 2005009961 A2, WO 2003047579, WO 2005094830, WO 2006089150, WO 2006125539, WO 2006057998 and WO 2007053574.

Suitable second therapeutic agents are those agent useful in the treatment or prevention of a disease or condition selected from cancer, viral infections, inflammatory disorders (e.g., inflammatory disorders of the skin, eye and/or ear), diabetic neuropathy, pulmonary hypertension, arterial restenosis, osteoporosis and transplant rejection.

Preferably, the second therapeutic agent is an agent useful in the treatment or prevention of a disease or condition selected from renal cell carcinoma and various cancers including liver, non-small cell lung, lung, breast, ovarian, fallopian tube, peritoneal cavity, pancreatic, bladder, metastatic prostate, thyroid, uterine, gastrointestinal stromal, metastatic melanoma, prostate adenocarcinoma, soft tissue sarcoma, mesothelioma, glioblastoma multiforme, acute myeloid leukemia, non-Hodgkin's lymphoma, multiple myeloma, glioblastoma, lymphoma, anaplastic astrocytoma, solid tumor, colorectal, squamous cell head and neck carcinoma, and oligodendroglioma; pulmonary hypertension; osteoporosis; and inflammatory disorders.

In one embodiment, the second therapeutic agent is selected from doxorubicin, dacarbazine, temozolomide, anastrozole, gemcitabine, topotecan, bicalutamide, RAD001, AMG 386, taxotere, bevacizumab, temsirolimus, erlotinib, tipifarnib, perifosine, pemetrexed, cetuximab, recombinant IL-21, paclitaxel, irinotecan hydrochloride, everolimus, abraxane, mitoxantrone, prednisone, etoposide, cisplatin and carboplatin.

In another embodiment, the invention provides separate dosage forms of a compound of this invention and one or more of any of the above-described second therapeutic agents, wherein the compound and second therapeutic agent are associated with one another. The term "associated with one another" as used herein means that the separate dosage forms are packaged together or otherwise attached to one another such that it is readily apparent that the separate dosage forms are intended to be sold and administered together (within less than 24 hours of one another, consecutively or simultaneously).

In the pharmaceutical compositions of the invention, the compound of the present invention is present in an effective amount. As used herein, the term "effective amount" refers to an amount which, when administered in a proper dosing regimen, is sufficient to treat the target disorder.

The interrelationship of dosages for animals and humans (based on milligrams per meter squared of body surface) is described in Freireich et al., Cancer Chemother. Rep, 1966, 50: 219. Body surface area may be approximately determined from height and weight of the subject. See, e.g., Scientific Tables, Geigy Pharmaceuticals, Ardsley, N.Y., 1970, 537.

In one embodiment, an effective amount of a compound of this invention can range from about 0.5 to 6000 mg per treatment. In more specific embodiments the range is from about 5 to 3000 mg, or 10 to 1200 mg, or most specifically from about 50 to 600 mg per treatment. Treatment typically is administered from about twice daily to once per week.

Effective doses will also vary, as recognized by those skilled in the art, depending on the diseases treated, the severity of the disease, the route of administration, the sex, age and general health condition of the subject, excipient usage, the possibility of co-usage with other therapeutic treatments such as use of other agents and the judgment of the treating physician. For example, guidance for selecting an effective dose can be determined by reference to the prescribing information for sorafenib or BAY 73-4506.

For pharmaceutical compositions that comprise a second therapeutic agent, an effective amount of the second therapeutic agent is between about 20% and 100% of the dosage normally utilized in a monotherapy regime using just that agent. Preferably, an effective amount is between about 70% and 100% of the normal monotherapeutic dose. The normal monotherapeutic dosages of these second therapeutic agents are well known in the art. See, e.g., Wells et al., eds., Pharmacotherapy Handbook, 2nd Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000), each of which references are incorporated herein by reference in their entirety.

It is expected that some of the second therapeutic agents referenced above will act synergistically with the compounds of this invention. When this occurs, it will allow the effective dosage of the second therapeutic agent and/or the compound of this invention to be reduced from that required in a monotherapy. This has the advantage of minimizing toxic side effects of either the second therapeutic agent of a compound of this invention, synergistic improvements in efficacy, improved ease of administration or use and/or reduced overall expense of compound preparation or formulation.

Methods of Treatment

In another embodiment, the invention provides a method of inhibiting multiple kinases in a cell, comprising contacting a cell with one or more compounds of Formula I, IA or IB herein.

For each of the methods of treatment disclosed herein, the subject being treated may be, for example, a patient in need of the treatment.

According to another embodiment, the invention provides a method of treating a disease that is beneficially treated by sorafenib or BAY 73-4506 in a subject, comprising the step of administering to the subject an effective amount of a compound or a composition of this invention. Such diseases are well known in the art and are disclosed in, but not limited to the following patents and published applications: WO 2005009961 A2, WO 2005000284, WO 2007068383, WO 2007068381, WO 2007053573, WO 2007054302, WO 2007054215. Such diseases include, but are not limited to, cancer, viral infections, inflammatory disorders (e.g., inflammatory disorders of the skin, eye and/or ear), diabetic neuropathy, pulmonary hypertension, arterial restenosis, osteoporosis and transplant rejection.

In one embodiment, the method of this invention is used to treat a disease or condition selected from renal cell carcinoma and various cancers including liver, non-small cell lung, lung, breast, ovarian, fallopian tube, peritoneal cavity, pancreatic, bladder, metastatic prostate, thyroid, uterine, gastrointestinal stromal, metastatic melanoma, prostate adenocarcinoma, soft tissue sarcoma, mesothelioma, glioblastoma multiforme, acute myeloid leukemia, non-Hodgkin's lymphoma, multiple myeloma, glioblastoma, lymphoma, anaplastic astrocytoma, solid tumor, colorectal, squamous cell head and neck carcinoma, and oligodendroglioma; pulmonary hypertension; osteoporosis; and inflammatory disorders.

In one particular embodiment, the method of this invention is used to treat a disease or condition selected from renal cell carcinoma and other cancers including liver, non-small cell lung, lung, breast, ovarian, fallopian tube, peritoneal cavity, pancreatic, bladder, prostate metastatic, thyroid, uterine, gastrointestinal stromal, metastatic melanoma, prostate adenocarcinoma, soft tissue sarcoma, mesothelioma, glioblastoma multiforme, acute myeloid leukemia, non-Hodgkin's lymphoma, multiple myeloma, glioblastoma, lymphoma, anaplastic astrocytoma, squamous cell head and neck carcinoma, oligodendroglioma, solid tumor, and colorectal cancers, and pulmonary hypertension in a subject.

In another particular embodiment, the method of this invention is used to treat renal cell carcinoma in a subject.

Identifying a subject can be in the judgment of a patient or a health care professional and can be subjective (e.g. opinion) or objective (e.g. measurable by a test or diagnostic method).

In another embodiment, any of the above methods of treatment comprises the further step of co-administering to the subject one or more second therapeutic agents. The choice of second therapeutic agent may be made from any second therapeutic agent known to be useful for co-administration with sorafenib or BAY 73-4506. The choice of second therapeutic agent is also dependent upon the particular disease or condition to be treated. Examples of second therapeutic agents that may be employed in the methods of this invention are those set forth above for use in combination compositions comprising a compound of this invention and a second therapeutic agent.

In one embodiment, the invention provides a method of treating renal cell carcinoma, comprising the step of co-administering to a subject: (a) a compound of Formula I, IA or IB, a pharmaceutically acceptable salt of a compound of Formula I, IA or IB or a pharmaceutical composition comprising either of the foregoing; and (b) a second therapeutic agent selected from AMG 386, recombinant IL-21, perifosine, and RAD001.

In another embodiment, the invention provides a method of treating hepatocellular carcinoma, comprising the step of co-administering to a subject: (a) a compound of Formula I, IA or IB, a pharmaceutically acceptable salt of a compound of Formula I, IA or IB, or a pharmaceutical composition comprising either of the foregoing; and (b) doxorubicin.

In another embodiment, the invention provides a method of treating breast cancer, comprising the step of co-administering to a subject: (a) a compound of Formula I, IA or IB, a pharmaceutically acceptable salt of a compound of Formula I, IA or IB, or a pharmaceutical composition comprising either of the foregoing; and (b) anastrozole.

In yet another embodiment, the invention provides a method of treating bladder cancer, comprising the step of co-administering to a subject: (a) a compound of Formula I, IA or IB, a pharmaceutically acceptable salt of a compound of Formula I, IA or IB, or a pharmaceutical composition comprising either of the foregoing; and (b) a second therapeutic agent selected from gemcitabine and carboplatin.

In another embodiment, the invention provides a method of treating pancreatic cancer, comprising the step of co-administering to a subject: (a) a compound of Formula I, IA or IB, a pharmaceutically acceptable salt of a compound of Formula I, IA or IB, or a pharmaceutical composition comprising either of the foregoing; and (b) gemcitabine.

In still another embodiment, the invention provides a method of treating small cell lung cancer, comprising the step of co-administering to a subject: (a) a compound of Formula I, IA or IB, a pharmaceutically acceptable salt of a compound of Formula I, IA or IB, or a pharmaceutical composition comprising either of the foregoing; and (b) topotecan.

In another embodiment, the invention provides a method of treating non-small cell lung cancer, comprising the step of co-administering to a subject: (a) a compound of Formula I, IA or IB, a pharmaceutically acceptable salt of a compound of Formula I, IA or IB, or a pharmaceutical composition comprising either of the foregoing; and (b) a second therapeutic agent selected from pemetrexed, carboplatin, gemcitabine, cisplatin, and etoposide.

In an alternate embodiment, the invention provides a method of treating prostate adenocarcinoma, comprising the step of co-administering to a subject: (a) a compound of Formula I, IA or IB, a pharmaceutically acceptable salt of a compound of Formula I, IA or IB, or a pharmaceutical composition comprising either of the foregoing; and (b) bicalutamide.

In yet another embodiment, the invention provides a method of treating kidney cancer, comprising the step of co-administering to a subject: (a) a compound of Formula I, IA or IB, a pharmaceutically acceptable salt of a compound of Formula I, IA or IB, or a pharmaceutical composition comprising either of the foregoing; and (b) a second therapeutic agent selected from RAD001, bevacizumab, and temsirolimus.

In still another embodiment, the invention provides a method of treating prostate cancer, comprising the step of co-administering to a subject: (a) a compound of Formula I, IA or IB, a pharmaceutically acceptable salt of a compound of Formula I, IA or IB, or a pharmaceutical composition comprising either of the foregoing; and (b) a second therapeutic agent selected from taxotere, mitoxantrone, and prednisone.

In a separate embodiment, the invention provides a method of treating brain or central nervous system tumors, comprising the step of co-administering to a subject: (a) a compound of Formula I, IA or IB, a pharmaceutically acceptable salt of a compound of Formula I, IA or IB, or a pharmaceutical composition comprising either of the foregoing; and (b) a second therapeutic agent selected from erlotinib, tipifarnib, and temsirolimus.

In another separate embodiment, the invention provides a method of treating colorectal cancer, comprising the step of co-administering to a subject: (a) a compound of Formula I, IA or IB, a pharmaceutically acceptable salt of a compound of Formula I, IA or IB, or a pharmaceutical composition comprising either of the foregoing; and (b) a second therapeutic agent selected from cetuximab, and irinotecan hydrochloride.

In another embodiment, the invention provides a method of treating intraocular melanoma, comprising the step of co-administering to a subject: (a) a compound of Formula I, IA or IB, a pharmaceutically acceptable salt of a compound of Formula I, IA or IB, or a pharmaceutical composition comprising either of the foregoing; and (b) a second therapeutic agent selected from paclitaxel, and carboplatin.

In a different embodiment, the invention provides a method of treating solid tumors, comprising the step of co-administering to a subject: (a) a compound of Formula I, IA or IB, a pharmaceutically acceptable salt of a compound of Formula I, IA or IB, or a pharmaceutical composition comprising either of the foregoing; and (b) a second therapeutic agent selected from temsirolimus, erlotinib, and bevacizumab.

In another embodiment, the invention provides a method of treating melanoma, comprising the step of co-administering to a subject: (a) a compound of Formula I, IA or IB, a pharmaceutically acceptable salt of a compound of Formula I, IA or IB, or a pharmaceutical composition comprising either of the foregoing; and (b) a second therapeutic agent selected from temsirolimus, abraxane, carboplatin, dacarbazine, and temozolomide.

In yet another embodiment, the invention provides a method of treating lymphoma or multiple myeloma, comprising the step of co-administering to a subject: (a) a compound of Formula I, IA or IB, a pharmaceutically acceptable salt of a compound of Formula I, IA or IB, or a pharmaceutical composition comprising either of the foregoing; and (b) everolimus.

The term "co-administered" as used herein means that the second therapeutic agent may be administered together with a compound of this invention as part of a single dosage form (such as a composition of this invention comprising a compound of the invention and an second therapeutic agent as described above) or as separate, multiple dosage forms. Alternatively, the additional agent may be administered prior to, consecutively with, or following the administration of a compound of this invention. In such combination therapy treatment, both the compounds of this invention and the second therapeutic agent(s) are administered by conventional methods. The administration of a composition of this invention, comprising both a compound of the invention and a second therapeutic agent, to a subject does not preclude the separate administration of that same therapeutic agent, any other second therapeutic agent or any compound of this invention to said subject at another time during a course of treatment.

Effective amounts of these second therapeutic agents are well known to those skilled in the art and guidance for dosing may be found in patents and published patent applications referenced herein, as well as in Wells et al., eds., Pharmacotherapy Handbook, 2nd Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000), and other medical texts. However, it is well within the skilled artisan's purview to determine the second therapeutic agent's optimal effective-amount range.

In one embodiment of the invention, where a second therapeutic agent is administered to a subject, the effective amount of the compound of this invention is less than its effective amount would be where the second therapeutic agent is not administered. In another embodiment, the effective amount of the second therapeutic agent is less than its effective amount would be where the compound of this invention is not administered. In this way, undesired side effects associated with high doses of either agent may be minimized. Other potential advantages (including without limitation improved dosing regimens and/or reduced drug cost) will be apparent to those of skill in the art.

In yet another aspect, the invention provides the use of a compound of Formula I (i.e., I, IA or IB) or a pharmaceutically acceptable salt thereof, alone or together with one or more of the above-described second therapeutic agents in the manufacture of a medicament, either as a single composition or as separate dosage forms, for treatment in a subject of a disease, disorder or symptom set forth above. Another aspect of the invention is a compound of Formula I (i.e., I, IA or IB) or a pharmaceutically acceptable salt thereof, for use in the treatment or prevention in a subject of a disease, disorder or symptom thereof delineated herein.

EXAMPLES

Example 1

Synthesis of 4-Chloro-2,3,5-d$_3$-picolinoyl chloride hydrochloride (11-d3)

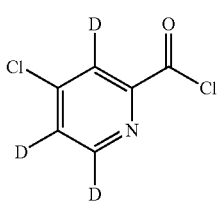

11-d3

To a round-bottom flask was added 2,3,4,5-d$_4$-picolinic-acid (10-d4; 400 mg, 3.15 mmol; CDN), thionyl chloride (4.0 mL), sodium bromide (96 mg, 0.933 mmol) and DMF (0.080 mL). The mixture was heated at reflux for 72 h. Upon cooling to room temperature, the reaction was diluted with toluene and concentrated in vacuo. The work-up was repeated one more time and then the crude material was placed under high vacuum for several hours to afford 11-d3 as a brown solid. MS (M+MeOH—Cl): 174.9.

Example 2

Synthesis of 4-Chloro-N-(methyl-d$_3$)-2,3,5-d$_3$-picolinamide (12-d6)

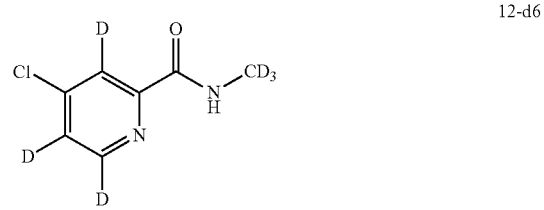 [SMILES: [2H]c1nc(C(=O)NC([2H])([2H])[2H])c([2H])c(Cl)c1[2H]]

12-d6

To a solution of sodium carbonate (3.33 g, 31.4 mmol) in water (10 mL) at 0° C. was added d3-methylamine hydrochloride (1.77 g, 25.1 mmol; 98 atom % D methylamine hydrochloride (Cambridge Isotopes Laboratories)). The resulting solution was added via cannula to a solution of 11-d3 (approximately 3.15 mmol) in methylene chloride (10 mL) at 0° C. The resulting mixture was allowed to warm to rt. After stirring overnight, the reaction was diluted with EtOAc and saturated aqueous sodium bicarbonate. The organic layer was washed twice with saturated aqueous sodium bicarbonate and the combined aqueous solutions were back-extracted once with EtOAc. The combined organic solutions were dried over Na$_2$SO$_4$, filtered and concentrated in vacuo. Purification via column chromatography on an ISCO instrument (0% to 30% EtOAc in hexane) provided 2.58 g (46%) of 12-d6. MS (M+H): 176.9.

Example 3

Synthesis of 4-(4-Amino(phenoxy-d$_4$))-N-(methyl-d$_3$)-2,3,5-d$_3$-picolinamide (14-d10)

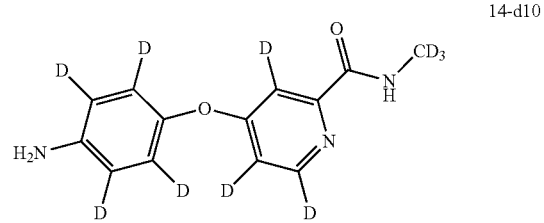 [SMILES: [2H]c1nc(C(=O)NC([2H])([2H])[2H])c([2H])c(Oc2c([2H])c([2H])c(N)c([2H])c2[2H])c1[2H]]

14-d10

To a solution of d7-4-aminophenol (13-d7; 222 mg, 1.91 mmol; 97 atom % D (CDN Isotopes)) in DMF (2.0 mL) was added potassium tert-butoxide (222 mg, 1.98 mmol). The reaction was stirred for 1 h, whereupon a solution of 12-d6 (305 mg, 1.73 mmol) in DMF (0.6 mL) was added via cannula, followed by a 0.6 mL DMF rinse. K$_2$CO$_3$ (129 mg, 0.935 mmol) was added and the mixture was heated to 80° C. for 12 h. The reaction was then cooled to rt, diluted with EtOAc, and poured into a separatory funnel containing EtOAc and brine. The organic layer was washed twice with brine. The combined aqueous solutions were washed once with EtOAc, and the combined organic solutions were dried over Na$_2$SO$_4$, filtered and concentrated in vacuo. Purification on an ISCO instrument (0% to 90% EtOAc in hexanes) afforded 381 mg (87%) of 14-d10. MS (M+H): 254.0.

Example 4

Synthesis of 2,6-d$_2$-Chloro-3-(trifluoromethyl) aniline (15-d2)

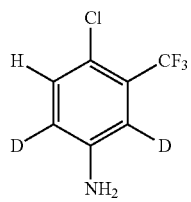

15-d2

To a pressure tube were added 4-chloro-3-(trifluoromethyl)aniline (1.08 g, 5.52 mmol), D$_2$O (1 mL; 99.9 atom % D deuterium oxide (Cambridge Isotopes)), and DCl (35 wt % in D$_2$O, 0.268 mL, 6.06 mmol; 99 atom % D DCl in D$_2$O (Sigma-Aldrich)) under N$_2$. The tube was sealed and heated at 160° C. for 16 hours (h). The mixture was then cooled to room temperature (rt), and the resulting solid was treated with 1N NaOH and EtOAc and stirred manually until a biphasic homogeneous solution resulted. The layers were separated and the organic layer was washed once with 1N NaOH. The combined aqueous solutions were washed once with EtOAc. The combined organic layers were dried (Na$_2$SO$_4$) and concentrated to dryness. The unpurified material thus obtained was subjected to two more cycles of heating to 160° C., cooling, washing and drying. The second heating was for 48 h. The third heating was for 16 h. The unpurified material obtained after the third cycle was added to a microwave tube, followed by D$_2$O (1 mL), and DCl (35 wt % in D$_2$O, 0.32 mL, 7.24 mmol) under N$_2$. The mixture was heated by microwave irradiation at 200° C. for 2 h 5 minutes (min) and then submitted to the work-up procedure described above. Purification on an ISCO instrument (40 g SiO$_2$, 0 to 30% EtOAc in hexanes) afforded 487 mg (49%) of 15-d2 as a pale yellow solid. The percentage of material undeuterated at the 2 and 6 positions was calculated to be 9% by $^1$H NMR analysis. MS (M+H): 197.9.

Example 4

Evaluation of Metabolic Stability

Microsomal Assay

Human liver microsomes (20 mg/mL) are obtained from Xenotech, LLC (Lenexa, Kans.). β-nicotinamide adenine dinucleotide phosphate, reduced form (NADPH), magnesium chloride (MgCl$_2$), and dimethyl sulfoxide (DMSO) are purchased from Sigma-Aldrich.

Determination of Metabolic Stability 7.5 mM stock solutions of test compounds are prepared in DMSO. The 7.5 mM stock solutions are diluted to 12.5 μM in acetonitrile (ACN). The 20 mg/mL human liver microsomes are diluted to 0.625 mg/mL in 0.1 M potassium phosphate buffer, pH 7.4, containing 3 mM MgCl$_2$. The diluted microsomes are added to wells of a 96-well deep-well polypropylene plate in triplicate. A 10 μL aliquot of the 12.5 μM test compound is added to the microsomes and the mixture is pre-warmed for 10 minutes. Reactions are initiated by addition of pre-warmed NADPH solution. The final reaction volume is 0.5 mL and contains 0.5 mg/mL human liver microsomes, 0.25 μM test compound, and 2 mM NADPH in 0.1 M potassium phosphate buffer, pH 7.4, and 3 mM MgCl$_2$. The reaction mixtures are incubated at 37° C., and 50 μL aliquots are removed at 0, 5, 10, 20, and 30 minutes and added to shallow-well 96-well plates which contain 50 μL of ice-cold ACN with internal standard to stop the reactions. The plates are stored at 4° C. for 20 minutes after which 100 μL of water is added to the wells of the plate before centrifugation to pellet precipitated proteins. Supernatants are transferred to another 96-well plate and analyzed for amounts of parent remaining by LC-MS/MS using an Applied Bio-systems API 4000 mass spectrometer. The same procedure is followed for sorafenib or BAY 73-4506 and the positive control, 7-ethoxycoumarin (1 μM). Testing is done in triplicate.

Data Analysis

The in vitro $t_{1/2}$s for test compounds are calculated from the slopes of the linear regression of % parent remaining (ln) vs incubation time relationship.

$$\text{in vitro } t_{1/2} = 0.693/k$$

$k = -$[slope of linear regression of % parent remaining (ln) vs incubation time]

Data analysis is performed using Microsoft Excel Software.

Without further description, it is believed that one of ordinary skill in the art can, using the preceding description and the illustrative examples, make and utilize the compounds of the present invention and practice the claimed methods. It should be understood that the foregoing discussion and examples merely present a detailed description of certain preferred embodiments. It will be apparent to those of ordinary skill in the art that various modifications and equivalents can be made without departing from the spirit and scope of the invention.

We claim:
1. A compound of Formula IA:

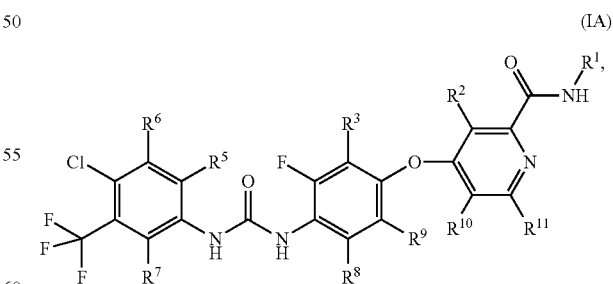

(IA)

or a pharmaceutically acceptable salt thereof, wherein:
R$^1$ is selected from CH$_3$ and CD$_3$;
R$^2$, R$^{10}$ and R$^{11}$ are simultaneously D or H;
R$^3$, R$^8$ and R$^9$ are simultaneously D or H; and
R$^5$, R$^6$ and R$^7$ are simultaneously D or H,
wherein at least one R group comprises a deuterium atom.

2. The compound of claim 1 having the formula IA, wherein the compound is selected from any one of the compounds set forth in the table below:

| Compound | $R^1$ | $R^2$ | $R^3$ | $R^5$ | $R^6$ | $R^7$ | $R^8$ | $R^9$ | $R^{10}$ | $R^{11}$ |
|---|---|---|---|---|---|---|---|---|---|---|
| 100 | $CH_3$ | D | D | D | D | D | D | D | D | D |
| 101 | $CH_3$ | H | D | D | D | D | D | D | H | H |
| 102 | $CH_3$ | D | H | D | D | D | H | H | D | D |
| 103 | $CH_3$ | D | D | H | H | H | D | D | D | D |
| 104 | $CH_3$ | H | H | D | D | D | H | H | H | H |
| 105 | $CH_3$ | H | D | H | H | H | D | D | H | H |
| 106 | $CH_3$ | D | H | H | H | H | H | H | D | D |
| 107 | $CD_3$ | D | D | D | D | D | D | D | D | D |
| 108 | $CD_3$ | H | D | D | D | D | D | D | H | H |
| 109 | $CD_3$ | D | H | D | D | D | H | H | D | D |
| 110 | $CD_3$ | D | D | H | H | H | D | D | D | D |
| 111 | $CD_3$ | H | H | D | D | D | H | H | H | H |
| 112 | $CD_3$ | H | D | H | H | H | D | D | H | H |
| 113 | $CD_3$ | D | H | H | H | H | H | H | D | D |
| 114 | $CD_3$ | H | H | H | H | H | H | H | H | H | or a pharmaceutically acceptable salt thereof.

3. The compound of claim 1, wherein any atom not designated as deuterium is present at its natural isotopic abundance.

4. A pyrogen-free pharmaceutical composition comprising a compound of claim 1 or a pharmaceutically acceptable salt thereof; and a pharmaceutically acceptable carrier.

5. The composition of claim 4, additionally comprising a second therapeutic agent useful in the treatment of a disease or condition selected from renal cell carcinoma and other cancers including liver, non-small cell lung, lung, breast, ovarian, fallopian tube, peritoneal cavity, pancreatic, bladder, prostate metastatic, thyroid, uterine, gastrointestinal stromal, metastatic melanoma, prostate adenocarcinoma, soft tissue sarcoma, mesothelioma, glioblastoma multiforme, acute myeloid leukemia, non-Hodgkin's lymphoma, multiple myeloma, glioblastoma, lymphoma, anaplastic astrocytoma, squamous cell head and neck carcinoma, oligodendroglioma, solid tumor, and colorectal cancers, viral infections, inflammatory disorders, diabetic neuropathy, pulmonary hypertension, arterial restenosis, osteoporosis and transplant rejection.

6. The composition of claim 5, wherein the second therapeutic agent is selected from doxorubicin, dacarbazine, temozolomide, anastrozole, gemcitabine, topotecan, bicalutamide, RAD001, AMG 386, taxotere, bevacizumab, temsirolimus, erlotinib, tipifarnib, perifosine, pemetrexed, cetuximab, recombinant IL-21, paclitaxel, irinotecan hydrochloride, everolimus, abraxane, mitoxantrone, prednisone, etoposide, cisplatin and carboplatin.

7. A method of treating a disease or condition selected from renal cell carcinoma and other cancers including liver, non-small cell lung, lung, breast, ovarian, fallopian tube, peritoneal cavity, pancreatic, bladder, prostate metastatic, thyroid, uterine, gastrointestinal stromal, metastatic melanoma, prostate adenocarcinoma, soft tissue sarcoma, mesothelioma, glioblastoma multiforme, acute myeloid leukemia, non-Hodgkin's lymphoma, multiple myeloma, glioblastoma, lymphoma, anaplastic astrocytoma, squamous cell head and neck carcinoma, oligodendroglioma, solid tumor, and colorectal cancers, viral infections, inflammatory skin, eye and/or ear diseases, diabetic neuropathy, pulmonary hypertension, arterial restenosis, osteoporosis and transplant rejection, in a subject the method comprising the step of administering to the subject an effective amount of a composition of claim 4.

8. The method of claim 7, wherein the disease or condition is renal cell carcinoma.

9. The method of claim 7, comprising the additional step of co-administering to the subject a second therapeutic agent useful in the treatment of a disease or condition selected from renal cell carcinoma, hepatocellular carcinoma, breast cancer, bladder cancer, pancreatic cancer, small cell lung cancer, non-small cell lung cancer, prostate adenocarcinoma, kidney cancer, prostate cancer, brain and central nervous system tumors, colorectal cancer, intraocular melanoma, solid tumors, melanoma, lymphoma or multiple myeloma, viral infections, inflammatory skin, eye and/or ear diseases, diabetic neuropathy, pulmonary hypertension, arterial restenosis, osteoporosis and transplant rejection.

10. The method of claim 9, wherein:
a. the second therapeutic reagent is selected from AMG 386, recombinant IL-21, perifosine, and RAD001; or
b. the second therapeutic reagent is doxorubicin; or
c. the second therapeutic reagent is anastrozole; or
d. the second therapeutic reagent is selected from gemcitabine and carboplatin; or
e. the second therapeutic reagent is gemcitabine; or
f. the second therapeutic reagent is topotecan; or
g. the second therapeutic reagent is selected from pemetrexed, carboplatin, gemcitabine, cisplatin, and etoposide; or
h. the second therapeutic reagent is bicalutamide; or
i. the second therapeutic reagent is selected from RAD001, bevacizumab, and temsirolimus; or
j. the second therapeutic reagent is selected from taxotere, mitoxantrone, and prednisone; or
k. the second therapeutic reagent is selected from erlotinib, tipifarnib, and temsirolimus; or
l. the second therapeutic reagent is selected from cetuximab and irinotecan hydrochloride; or
m. the second therapeutic reagent is selected from paclitaxel and carboplatin; or
n. the second therapeutic reagent is selected from temsirolimus, erlotinib, and bevacizumab; or
o. the second therapeutic reagent is selected from temsirolimus, abraxane, carboplatin, dacarbazine, and temozolomide; or
p. the second therapeutic reagent is everolimus.

* * * * *